United States Patent [19]
van de Ven et al.

[11] Patent Number: 5,989,856
[45] Date of Patent: Nov. 23, 1999

[54] PHARMACEUTICAL COMPOSITION HAVING AN ENDOPROTEOLYTIC ACTIVITY; A PROCESS FOR ENDOPROTEOLYTICALLY PROCESSING (PRECURSOR) PROTEINS AND FOR THE (MICRO)BIOLOGICAL PRODUCTION OF PROTEINS

[75] Inventors: Willem Jan van de Ven, St.Joris-Weert, Belgium; Anna Maria van den Ouweland, Randwijk, Netherlands; Johannes Lambertus van Duijnhoven, Helmond, Netherlands; Antonius Johannes Roebroek, Born, Netherlands; Piet Nico Koning, Oegstgeest, Netherlands

[73] Assignee: Katholieke Universiteit Leuven, Leuven, Belgium

[21] Appl. No.: 07/849,420

[22] PCT Filed: Oct. 12, 1990

[86] PCT No.: PCT/NL90/00151

§ 371 Date: Jun. 24, 1992

§ 102(e) Date: Jun. 24, 1992

[87] PCT Pub. No.: WO91/06314

PCT Pub. Date: May 16, 1991

[30] Foreign Application Priority Data

Oct. 25, 1989 [NL] Netherlands .......................... 8902651
Apr. 18, 1990 [NL] Netherlands .......................... 9000917

[51] Int. Cl.[6] .......................... A61K 38/48; C12P 21/06; C12N 9/64
[52] U.S. Cl. .................. 435/68.1; 435/226; 435/240.2
[58] Field of Search .................... 435/68.1, 69.1, 435/320.1, 226, 219

[56] References Cited

PUBLICATIONS

Fuller et al Science 246 p. 482 Oct. 27, 1989.
Thim et al Proc Nat Acad Sci USA 83 p. 6766 1986.
Wise et al Proc Natl Acad Sci USA 87 p. 9378 1990.
Mizuno et al Biochem Biophys Res Comm 156 p. 246 1988.
Roebroek et al EMBO 5 p. 2197 1987.
Van den Ouweland et al NAR 17 p. 7101 1989.
Misumi et al NAR 18 p. 6719 1990.
Lehninger, Biochemistry, Worth Publishing, 1975.
Boehringer Mannheim Biochemical Cataloge p. 496.

*Primary Examiner*—Mindy B. Fleisher
*Assistant Examiner*—D. Schmickel
*Attorney, Agent, or Firm*—Cooper & Dunham LLP

[57] ABSTRACT

The invention is based on the finding that furin belongs to a family of endoproteolytically active enzymes and relates to a process for the in vitro cleavage of a protein by treating the protein in the presence of $Ca^{2+}$ ions with furin or furin like enzyme, or enzymatically active fragment, derivative or fusion protein of furin or furin-like enzyme.

34 Claims, 6 Drawing Sheets

MELRPWLLWVVAATGTLVLLAADAQGQKVFTNTWAV
RIPGGPAVANSVARKHGFLNLGQIFGDYYHFWHRGV
TKRSLSPHRPRHSRLQREPQVQWLEQQVAKRRTKRD
VYQEPTDPKFPQQWYLSGVTQRDLNVKAAWAQGYTG
HGIVVSILDDGIEKNHPDLAGNYDPGASFDVNDQDP
DPQPRYTQMNDNRHGTRCAGEVAAVANNGVCGVGVA
YNARIGGVRMLDGEVTDAVEARSLGLNPNHIHIYSA
SWGPEDDGKTVDGPARLAEEAFFRGVSQGRGGLGSI
FVWASGNGGREHDSCNCDGYTNSIYTLSISSATQFG
NVPWYSEACSSTLATTYSSGNQNEKQIVTTDLRQKC
TESHTGTSASAPLAAGIIALTLEANKNLTWRDMQHL
VVQTSKPAHLNANDWATNGVGRKVSHSYGYGLLDAG
AMVALAQNWTTVAPQRKCIIDILTEPKDIGKRLEVR
KTVTACLGEPNHITRLEHAQARLTLSYNRRGDLAIH
LVSPMGTRSTLLAARPHDYSADGFNDWAFMTTHSWD
EDPSGEWVLEIENTSEANNYGTLTKFTLVLYGTAPE
GLPVPPESSGCKTLTSSQACVVCEEGFSLHQKSCVQ
HCPPGFAPQVLDTHYSTENDVETIRASVCAPCHASC
ATCQGPALTDCLSCPSHASLDPVEQTCSRQSQSSRE
SPPQQQPPRLPPEVEAGQRLRAGLLPSHLPEVVAGL
SCAFIVLVFVTVFLVLQLRSGFSFRGVKVYTMDRGL
ISYKGLPPEAWQEECPSDSEEDEGRGERTAFIKDQS
AL

FIG. 1

```
               10          20          30          40          50
                .: :     .          .    :        :▼ ::    :...▼.... .::▼▼
hfur   DVYQEPTDPKF-PQQWYLSGVT--QRDLNVKAAWAQGY-TGHGIVVSILDDGIEKNHPDLAG   58
kex1   RILFNISDPLF-DQQWHLINPNYPGNDVNVTGLWKENI-TGYGVVAALVDDGLDYENEDLKD   60
kex2   EDKLSINDPLF-ERQWHLVNPSFPGSDINVLDLWYNNI-TGAGVVAAIVDDGLDYENEDLKD   60
ther   YTPNDPYFSSRQYGPQKIQ------APQAW-DIA-EGSGAKIAIVDTGVQSNHPDLAG     50
subC   AQ-----TVPYGIPLIK--------ADKVQAQGF-KGANVKVAVLDTGIQASHPDL--     42
subB   AQ-----SVPYGVSQIK--------APALHSQGY-TGSNVKVAVIDSGIDSSHPDL--     42
                   aaaaaa         aaaaa        tt ββββββ       sstt ββββββ
3D                                                   **            tt tt 60          70          80          90         100         110
                 :: ::. :.                 . .: ▼▼▼::▼▼ ▼▼         ▼:        ▼: :.  .::.
hfur   NYDPGASFDVNDQDPDPQPRYTQMNDNRHGTRCAGEVAAVANNGVCG--VGVAYNARIGGVRM   119
kex1   NFCVEGSWDFNDNNPLPKPR---LKDDYHGTRCAGEIAAFR-NDICG--VGVAYNSKVSGIRI   117
kex2   NFCAEGSWDFNDNTNLPKPR---LSDDYHGTRCAGEIAAkkGNNFCG--VGVGYNAKISGIRI   118
ther   --KVVGGWDFVDNDSTPQ------NGNGHGTHCAGIAAAVTNNSTGI-AGTAPKASILAVRV   103
subC   --NVVGGASFVAGE-AYN------TDGNGHGTHVAGTVAAL-DNTTGV-LGVAPSVSLYAVKV    94
subB   --KVAGGASMVPSETNPF------QDNNSHGTHVAGTVAAL-NNSIGV-LGVAPSASLYAVKV    95
        ββββββ tt                          <==Ca==>            <==Ca==>
3D                                            *                  sssaaaaaaaaaa    sssss 120         130         140         150         160         170
         ▼.  .   :. ..   :                 :  : .   :  :  .  :    :  ▼ .: .           :
hfur   LD--GEVTDAVEARSLGLNPNH-IHIYSASWG-PEDDGKTVDGPARLAEEAFFRGVSQGRGG   177
kex1   LS--GQITAEDEAASLIYGLDV-NDIYSCSWG-PSDDGKTMQAPDTLVKkAIIKGVTEGRDA   175
kex2   LS--GDITTEDEAASLIYGLDV-NDIYSCSWG-PADDGRHLQGPSDLVKkALVKGVTEGRDS   176
ther   LDNSGSGTWTAVANGITYAADQGAKVISLSLGGTVG-------NSGLQQAVNYAWNK----   153
subC   LNSSGSGTYSGIVSGIEWATTNGMDVINMSLGGPSG-------STAMKQAVDNAYAR----   144
subB   LGADSGSGQYSWIINGIEWAIANNMDVINMSLGGPSG-------SAALKAAVDKAVAS----   145
       *       *   aaaaaaaaaaaaaaaatt ββββββ                 *  ******      aaaaaaaaaaat
3D     tt
```

```
             180        190       200       210       220       230
              ►    .  ►  ►▼.▼.      :▼..    :  :::..  :.    .▼.      :..:
hfur    LGSIFVWASGNGGREHDSCNCDGYTNSIYT-LSISSATQFGNVPWYSE-ACSSTLATTYSSG 237
kex1    KGALYVFASGNGGMFGDSCNFDGYTNSIFS-ITVGAIDWKGLHPPYSE-SCSAVMVVTYSSG 235
kex2    KGAIYVFASGNGGTRGDNCNYDGYTNSIYS-ITIGAIDHKDLHPPYSE-GCSAVMAVTYSSG 236
ther    -GSVVVAAAGNAGNTAP-----NYPAYYSNAIAVASTDQNDNKSSFST-YGSVVDVAAPGS- 207
subC    -GVVVVAAAGNSGSSGNTNTI-GYPAKYDSVIAVGAVDSNSNRASFSS-VGAELEVMAPGA- 202
subB    -GVVVVAAAGNEGTSGSSSTV-GYPGKYPSVIAVGAVDSSNQRASFSS-VGPELDVMAPGV- 203
            *   * ***                *                                *
3D      t ββββ                        ttt tt βββββ tt      tt  ββββ s 240       250       260       270       280       290
              . ::        ::    .▼▼▼ .;.▼.   ..▼     .▼.▼:.  ::.::   ..:
hfur    NQNEKQIVTTDLRQKCTESHTGTSASAPLAAGIIALTLEANKNLTWRDMQHLVVQTSKPAHL 298
kex1    SGN--YIKTTDLDEKCSNTHGGTSAAAPLAAGIYTLVLEANPNLTWRDVQYLSILSSEEINP 294
kex2    SGE--YIHSSDINGRCSNSHGGTSAAAPLAAGVYTLLLEANPNLTWRDVQYLSILSAVGLEK 295
ther    ----WIYSTYP-TSTYASLSGTSMATPHVAGVAGLLASQ--GRSASNIRAAJENTADKISG 262
subC    ------GVYSTYP-TSTYATLNGTSMASPHVAGAAAALILSKHPNLSASQVRNRLSSTATYLGS 258
subB    ------SIQSTLP-GNKYGAYNGTSMASPHVAGAAAALILSKHPNWTNTQVRSSLENTTTKLGD 259
                      *      ** ****
3D      sββββββt ttβββββ         aaaaaaaaaaaaaa     aaaaaaaaaaa 300       310       320       330       340       350
              .: ::    .▼              ::   ..:
hfur    NAN-DWATNGVGrKVSHSYGYGLLDAGAMVALAQNWTTVAPQrkCIIDILTEPKDIGkr-  (330)
kex1    H-DGKWQDTAMGKrYSHTYGFGKLDAYNIVHMAKSWINVNPQGWLYLPTIVEKQSISNS-  (221)
kex2    NADGDWRDSAMGKkYSHRYGFGKIDAHKLIEMSKTWENVNAQTWFYLPTLYVSQSTNST-  (322)
ther    --------------GTYWAKGRVNAYKAVQY                              279
subC    --------------SFYYGKGLINVEAAAQ                               274
subB    --------------SFYYGKGLINVQAAAQ                               275

3D                    aaaaa
```

FIG.3

Furin catalytic domain model

- ■ position of insert relative to subtilisin
- ⊏⊐ C-terminal extension (other domains)
- ⊥ negatively charged side chain
- ● Ca-ion
- ○ active site residues Asp46, His87, Ser261
- ••••• disulfide bridge

PHARMACEUTICAL COMPOSITION HAVING AN ENDOPROTEOLYTIC ACTIVITY; A PROCESS FOR ENDOPROTEOLYTICALLY PROCESSING (PRECURSOR) PROTEINS AND FOR THE (MICRO)BIOLOGICAL PRODUCTION OF PROTEINS

The invention relates to both a pharmaceutical composition having an endoproteolytic activity and a process for the (micro)biological production of a protein and for the in vitro cleavage of a protein, in particular a precursor protein by processing the protein with an endoproteolytically active enzyme.

The invention described herein is the result of a further study into the possible physiological significance of furin, a human protein described in European patent application EP-A-0 246 709, which is the expression product of the fur gene located in the genome upstream of the human fes/fps proto-oncogene. The patent application referred to and other publications by the same research group (Roebroek et al., Molec.Biol.Rep. 11, 1986, 117–125; Roebroek et al., EMBO J. 5, 1986, 2197–2202; and Schalken et al., J.Clin. Invest. 80, 1987, 1545–1549) show that on the basis of the limited DNA data then available, it was impossible to determine the function of the product of the fur gene. What could be determined was that the furin is probably a membrane-associated protein which has a function in which certain recognition structures play a role. It was also observed at the time that the fur gene is expressed as a 4.5 kb mRNA in liver, kidney, spleen, thymus and brain, whereas the expression in lung tissue is very slight; in non-small-cell lung carcinomas, on the other hand, a highly increased expression was found to occur, on the ground of which the fur gene was suggested to have a utility as a tumor marker.

Within the framework of the above research, the complete nucleotide sequence of a genomic DNA fragment of about 21 kbp containing the fur gene has meanwhile been determined (Van den Ouweland et al., Nucl.Acids Res. 17, 1989, 7101–7102), while the nucleotide sequence of the corresponding fur cDNA has also been determined (Van den Ouweland et al., Nucl. Acids Res. 18, 1990, 664). On the basis thereof it is not possible for the fur gene to be completely characterized, at both the level of genomic organization structure and the level of the encoding sequences. From these encoding nucleotides sequences, the amino acid sequence of the furin can also be derived.

A computer analysis of this amino acid sequence has now surprisingly revealed that furin is highly similar to subtilisin-like proteases as encoded in yeast by the KEX1 gene of *Kluyveromyces lactis* and the KEX2 gene of *Saccharomyces cerevisiae,* and that furin is evidently the higher-eukaryotic form (found in Man and in animals, such as monkey, cat, rat, mouse, chicken and Drosophila) of these endoproteases. More specifically it has been found that the furin exhibits a certain degree of homology with the catalytic domain of the hitherto described bacterial subtilisins (about 20 enzymes), such as thermitase of *Thermoactinomyces vulgaris* and subtilisin BPN' of *Bacillus amyloliquefaciens,* and exhibits a striking high homology with subtilisin-like proteases, such as the expression product of the KEX1 gene of the yeast *Kluyveromyces lactis* and the expression product of the KEX2 gene of the yeast *Saccharomyces cerevisiae.* The furin Seq ID NO:2), which contains 794 amino acids, exhibits in the domain of the amino acids 97 to 577 an overall homology of about 80.0% with the amino acids 123–584 of the expression product of said KEX1 gene (i.e., 41.6% identical amino acids and 38.3% conservative substitutes) and an overall homology of about 78.9% with the amino acids 134–597 of the expression product of said KEX2 gene (i.e., 39.4% identical amino acids and 39.5% conservative substitutes). These amino acid regions of the yeast proteases comprise the subtilisin-like catalytic domains. The subtilisin-like domain of furin is situated in an amino-terminal furin fragment comprising the amino acids 108–464 (Seq ID NO:3).

With regard to the subtilisin-like proteases, reference is made to the following publications: Tanguy-Rougeau et al., FEBS Letters 234, 1988, 464–470; Mizuno et al., Biochem. Biophys. Res Commun. 156, 1988, 246–254; Meloun et al. FEBS Letters 183, 1985, 195–200; Marklan et al., J.Biol.Chem. 242, 1967, 5198–5211; Mizuno et al., Biochem. Biophys. Res. Commun. 159, 1989, 305–311; Bathurst et al., Science 235, 1987, 348–350; Thomas et al., Science 241, 1988, 226–230; Foster et al., Biochemistry 29, 1990 347–354; Fuller et al., PNAS USA 86, 1989, 1434–1438; Julius et al., Cell 37, 1984, 1075–1089; Bourbonnais et al., J.Biol.Chem. 263, 1988, 15342–15347; Cosman et al., Dev-.Biol. Stand. 69, 1988, 9–13; Schubert Wright et al., Nature 221, 1969, 235–242; Cunningham et al., Yeast 5, 1989, 25–33; Davidson et al., Nature 333, 1988, 93–96.

As shown by the above publications, it is especially the expression product of the KEX2 gene of the yeast species *Saccharomyces cerevisiae* which has been well studied and characterized. It is a membrane-associated, calcium ions dependent endopeptidase with an enzyme specificity for paired basic amino acid residues; substrate proteins are cleaved at the carboxyl site of pairs of basic amino acids containing arginine by this enzyme, which is to be defined here as a "restriction" endopeptidase (by analogy to the nomenclature in restriction endonucleases in which a given nucleotide sequence is determinative of the cleavage of the DNA). The location of the enzyme is probably in a structure of the Golgi complex. The subtilisin-like domain and the $Ca^{2+}$ activation sequences are in the aminoterminal part of the protein. In the yeast *Saccharomyces cerevisiae,* the endopeptidase is involved in the proteolytic processing of precursors of killer toxin and pairing pheromone alpha factor, i.e., of pro-killer toxin and pro-alpha factor. Furthermore, the endopeptidase is found to be capable of correctly cleaving the mouse neuroendocine-peptide precursor prepro-opiomelanocortin after introduction into certain mutant mammalian cell lines with disturbed proteolytic processing, and to be capable of processing proalbumin to mature albumin and to be capable of processing the precursor of the plasma C protein.

On the ground of the established similarities between the above known endopeptidases and the furin, it is postulated that the furin is a restriction endopeptidase which can be used for the processing of proteins, more specifically the processing of the precursor proteins of polypeptide hormones, growth factors, toxins, enzymes, or other types of biologically relevant proteins. In this connection, in vitro applications are conceivable on the one hand, and in vivo applications on the other, including an application within the framework of a therapeutic treatment. For such applications, the human furin may be more suitable than the above known endopeptidases of non-human origin, or more generally an animal "furin" may be more suitable than an endopeptidase from lower organisms. The same applies to analogues or relatives of furin not yet isolated, referred to herein as furin-like enzymes, belonging to a larger family of restriction-endoproteolytic enzymes of which furin is the first-found representative. The various members of this family will exhibit a high structural resemblance, although the sequence homology may be quite low, possibly as low as below 50% homology. Within this family, it will be possible to distinguish several enzyme classes, such as a group of furin-like enzymes involved in the processing of constitutively secreted proteins and a group of furin-like enzymes involved in the processing of proteins whose secretion is regulated (secretion through secretory granula). It is possible that each of these furin-like enzymes in characteristically expressed in a limited number of cell types in which the enzyme is active as a processing enzym. A limited degree of overlap between the cell and tissue distribution of these enzymes is also conceivable and could very well be responsible for the known phenomenon of cell type-dependent differential processing of precursors.

The pituitary proteins PC1 and PC2, described recently by Seidah et al., DNA and Cell Biol. 9, 1990, 415–424, constitute examples of such furin-like enzymes.

Through recombinant DNA techniques, it is possible to obtain large quantities of the protein furin. In prokaryotes, the fur gene can be expressed as a fusion protein with beta-galactosidase (pUR vector system) or the anthranilate synthetase (pATH vector system). Another possibility is the synthesis of the fusion protein glutathion-S-transferase-furin (pGEX). The advantage of this approach is that the furin can be split off by means of thrombin. The furin can also be synthesized as such in prokaryotes by placing the cDNA in the correct manner behind a suitable promotor. The pUR and pATH vector systems have been described in the European patent application referred to hereinbefore. pGEX is commercially available. Using the strong SV40 promotor, the fur cDNA can be expressed in suitable eukaryotic cells. In connection with glycosylation of the protein, this approach is preferred for certain purposes.

Furin can be purified by standard biochemical techniques in the presence of protease inhibitors. Furin is active in a relatively acidic medium with a pH of 5.5, as occurs in secretory granula, but the protein maintains its activity also at pH 7.5. By virtue of this, a 0.2 M sodium acetate buffer (pH 5.5) of Tris-HCl buffer (7.0) may be used in vitro. The activity of the enzyme furin depends on the presence of $Ca^{2+}$ ions. For the in vitro enzyme activity, a calcium concentration of 2–5 mM has been found to be optimal. The presence of metal chelators such as EDTA will greatly inhibit the activity of furin. Furthermore, the presence of heavy metal ions such as $Zn^{2+}$, $Hg^{2+}$ and $Cu^{2+}$ should be avoided. The substance o-phenanthrolin binds heavy metals except $Ca^{2+}$ and thus has no adverse effect on the enzymatic activity of furin. Low concentrations of phenyl methyl sulphonyl fluoride (PMSF) and diisopropyl fluorophosphate (DFP) up to 5 mM have no inhibitory effect. At higher concentrations of PMSF, the enzyme function is inhibited. An in vitro incubation for two hours at 37° C. is sufficient for the processing of the protein to be cleaved.

Furin can be used for the endoproteolytic processing of various proteins. This makes it possible, for example, for in vitro produced precursor proteins to be specifically cleaved to form biologically active compositions which may be used as additional agents for the treatment of diseases in which the precursors are not split or to an insufficient degree. Generally speaking, furin may be said to be suitable in the processing of biologically relevant proteins.

The protein furin may also find application as a medicament, so that patients deficient in an endoprotease may be treated by administering furin, so that an adequate processing of precursor proteins is yet possible. As a result, the cleavage products may perform their function, and it will be possible for any disturbingly high levels of precursor proteins to be reduced.

Furin is possibly also applicable for clearing depositions with substrate proteins in, for example, the blood circulation system, so that obstructions of vital organs may be remedied by the administration of furin.

Furin is further also applicable in the commercial production of all sorts of biologically active substances (e.g., other enzymes) if processing is a production step therein.

The invention relates in the first place to a pharmaceutical composition comprising one or more pharmaceutically acceptable carriers, diluents or adjuvants, as well as an endoproteolytically active amount of furin or a furin-like enzyme, or a fragment or derivative of furin or furin-like enzyme having an endoproteolytic activity.

The proteolytic activity is maintained when the carboxyterminal region with the transmembrane domain therein has been split off. Instead of the complete furin or furin-like enzyme, therefore, according to the invention, use can be made of a fragment of the enzyme which still contains the part responsible for the proteolytic activity. One suitable fragment is, for example, the furin fragment consisting of amino acids 108–464 (Seq ID NO:3).

The activity of the furin or furin-like enzyme, or of an endoproteolytically active fragment thereof, can further be manipulated by introducing mutations. The invention accordingly also extends to derivatives of furin or furin-like enzyme still having endoproteolytic activity.

According to a preferred embodiment according to the invention of such a pharmaceutical composition, the furin or the furin-like enzyme, or the fragment or derivative of furin or furin-like enzyme having endoproteolytic activity, used in the composition, has been obtained from prokaryotic or eukaryotic cells which through genetic engineering with recombinant DNA or RNA have acquired the ability of expressing the furin, furin-like enzyme, fragment or derivative of furin or furin-like enzyme, whether or not in the form of a fusion protein, while in case the furin, furin-like enzyme, fragment or derivative of furin or furin-like enzyme is produced by the cells as a fusion protein, the fusion protein has been processed to split off the furin, furin-like enzyme, fragment or derivative of furin or furin-like enzyme from the fusion protein.

Another possibility, however, is for the source of the furin or furin-like enzyme used to be cells which by nature are capable of producing the furin or furin-like enzyme, for example, a suitable tumor cell line.

A particularly preferred embodiment of the invention concerns a pharmaceutical composition containing furin itself.

An alternative particularly preferred embodiment of the invention concerns a pharmaceutical composition comprising an aminoterminal fragment of furin comprising at least the amino acids 108–464 of furin (Seq ID NO:3).

The invention further relates to a process for the in vitro cleavage of a protein by treating the protein with an endoproteolytically active enzyme, in which, in accordance with the present invention, the protein is treated in the presence of $Ca^{2+}$ ions with furin or a furin-like enzyme, or an endoproteolytically active fragment, derivative or fusion protein of furin or furin-like enzyme as the endoproteolytically active enzyme.

The treatment will commonly be carried out at physiologically occurring pH and temperature values, i.e., at a pH within the range of 4–9 at a temperature of about 37° C.

Preferably, the treatment is carried out at a pH of 5–7.5, more preferably 5.5–7.0.

Also, according to the invention, it is preferable for the treatment to be carried out at a temperature of 20–50° C., more preferably 30–40° C.

Furthermore, according to the invention, it is preferable for the treatment to be carried out at a calcium concentration of 1–10 mM, more preferably 2–5 mM.

According to a particularly preferred embodiment of the invention, the treatment is carried out in the presence of o-phenanthrolin or an equivalent agent for binding heavy metals other than calcium.

The process according to the invention comprises a treatment of a ;substrate to be processed as such with furin (or with a furin-like enzyme) as such, i.e., furin in an isolated or purified form, but also comprises a treatment with or within cells, in particular genetically engineered mammalian cells in which furin is expressed. Preferably, these are carefully selected, genetically engineered mammalian cells (such as COS-1 cells, CHO cells and endothelial cells) with high levels of expression of both the fur gene and a gene encoding for the substrate to be processed. As well known to those skilled in the art, a greatly enhanced expression can be realized by gene amplification or by using strong promotors. The invention even extends to applications involving transgenic animals, and is therefore not limited to in vitro protein production and protein cleaving processes. The invention accordingly also comprises mammalian cells and mammals comprising DNA originating from recombinant DNA encoding for furin or furin-like enzyme, and capable of expressing the furin or furin-like enzyme. Endothelial cells, for example, are particularly ideal as mammalian cells for transport of therapeutic genes and gene products through the body by reason of their distribution throughout the entire body (at the surface of blood vessels, lung tissue, and the like) and by virtue of their interaction with all sorts of components in the circulation of body fluids (the bloodstream and the like). Thus endothelial cells of a patient suffering from some disease resulting from a disturbance in the processing of pro-proteins, could be genetically engineered after being isolated from the body to remedy the defect by introducing an active fur gene, and subsequently the genetically modified cells could be re-transplanted into the patient. Such a gene therapy, however, is not limited to endothelial cells.

A preferred embodiment of the invention consists in a process for the (micro)biological production of a protein by culturing genetically engineered cells expressing a pro-form of the protein as well as furin, and possibly isolating the protein formed. For this purpose both prokaryotic and eukaryotic cells can be used, but cells of higher eukaryotes are preferred. For example, yeast cells or still better plant cells can be used. It is, however, particularly preferable to use genetically engineered mammalian cells.

The expression "pro-form" means a form of the protein which should or may be converted into the desired protein by processing. It may be a natural pro-form or prepro-form of the protein, but also a synthetic pro-form which is the result of a recombinant DNA construct in which the gene coding for the desired protein is preceded by an added signal or leader sequence.

As regards the substrates to be processed, generally speaking proteins with paired basic amino acid residues can serve as a substrate. The additional presence of basic amino acid residue in the −4 position relative to the cleavage site (i.e., 4 positions before the cleavage site) will lead to higher efficiency. The following examples are mentioned as possible substrates for processing by furin without completeness being pretended: precursors encoded by the transforming growth factor β (TGF-β) gene family of growth and differentiation factors (such as TGF-β1, TGF-β2, TGF-β3, TGF-β4, TGF-β5, activiv, inhibin, *Xenopus laevis* Vg1 gene product, Mullerian Inhibiting substance [MIS], decapentapeptide gene complex of Drosophila embryos and bone morphogenetic protein, see Sport and Roberts, Anal. N.Y. Acad. Sci. 593, 1990, 1–6), precursors of growth factors, such as β-Nerve Growth Factor (β-NGF) and insulin, precursors of clotting factors, such as von Willebrand Factor, Protein C, Factor IX and Factor X, hormones and neuropeptides, such as Proopio-melanocortin, Proenkephalin, Prodynorphin, Provasopressin, Prooxytocin, ProCRF (corticotropin releasing factor), ProGRF (growth hormone releasing factor), Prosomatostatin, Proglucagon, Procalcitonin, ProCGRP (calcitonin gene-related peptide), ProVIP (vasoactive intestinal peptide), Procaerulin and ProELH (egg laying hormone), interleukins, interferons, and hematopoietic factors.

The invention can also be applied to proteins which do not by themselves require endoproteolytic processing. Examples are gene constructs in which, for reasons of good processing (glycosylation) or ready purification (secretion) a sequence encoding for the desired protein is coupled to a suitable signal sequence, as has been proposed earlier, for example, for the production of erythropoietin in yeast cells by Elliott et al., Gene 79, 1989, 167–180. In that publication, a gene construct is described from the leader region of prepro-alpha factor placed before the erythropietin sequence. The processing of the resulting synthetic precursor is effected in the yeast cells by the KEX2 gene product present therein.

A further illustration of the invention will be given with reference to the accompanying drawings, in which

BRIEF DESCRIPTION OF DRAWINGS

FIG. 1 shows the amino acid sequence of furin (Seq ID No. 2).

FIG. 3 shows a comparison of the amino acid sequence of: furin (hfur) Seq ID No.3; Kex 1 protease (kex1) Seq ID No.4; Kex2 protease (Kex2) Seq ID No. 5; thermitase (ther) Seq ID No.6; subtilisin Carlsberg (subC) Seq ID No.7, and subtilisin BPN' (subB) Seq ID No. 8.

FIG. 1 shows the amino acid sequence (in the one-letter code) of the furin consisting of 794 amino acids (Seq ID NO:2).

FIG. 2 shows diagrammatically the furin gene, cDNA and protein.

Figure 2:
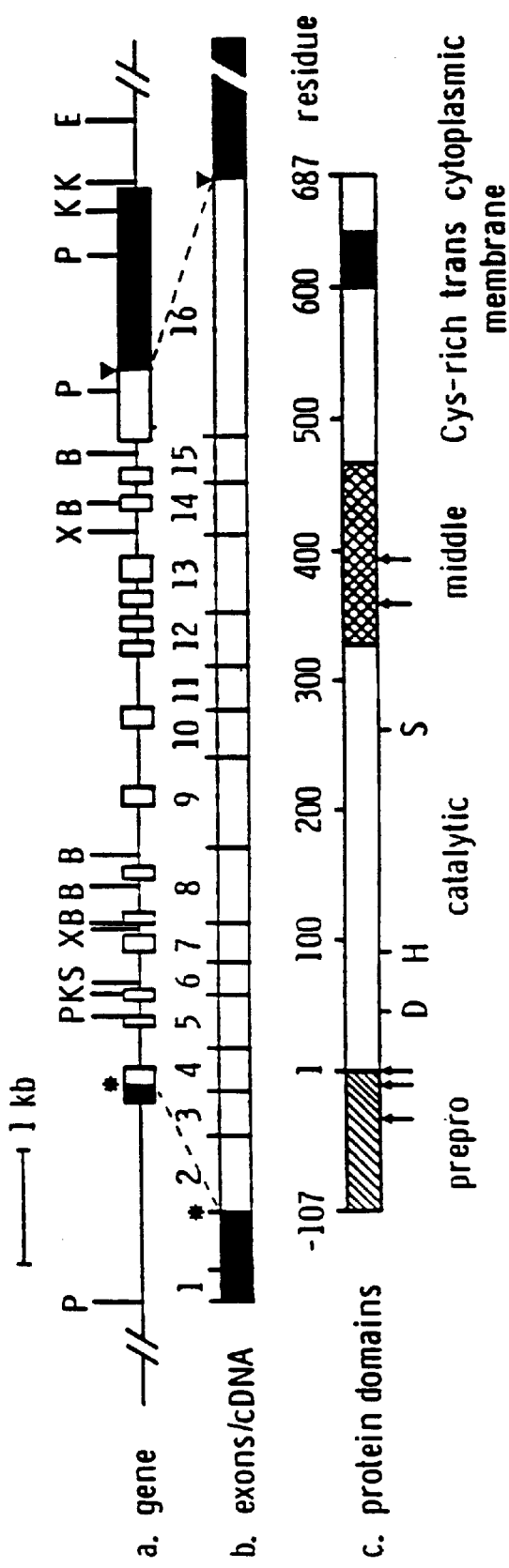
FIG. 2 shows furin's a. genomic organization; b. exon organization of the cDNA; c. functional organization of the protein.

a. Genomic organization of part of the fur gene. Exon 1 (about 120 bp) is located at 7.2 kb upstream of exon 2. The asterisk above exon 2 indicates the position of the initiation codon, and the arrow head above exon 16 the stop codon. Non-coding sequences are represented by black boxes. B=BamHI; E=EcoRI; K=KpnI; S=SalI; P=PstI; X=XbaI.

b. Schematic distribution of exons in the cDNA of fur.

c. The putative localization of the various protein domains in furin. The largest exon (exon 16) encodes nearly the entire Cys-rich domain, the transmembrane domain and the cytoplasmic domain. The exons 2–12 encode the presumptive prepro and catalytic domains, with codons for the active site residues Asp46 (D), His87 (H) and Ser261 (S) in exons 5, 7 and 10, respectively. This intron/exon distribution is of the same degree of complexity as observed in the trypsin family of serine proteases. Vertical arrows indicate pairs of basic residues (Arg—Arg, Lys—Arg) which are potential autoprocessing sites; the pairs of basic amino acid residues Arg310–Lys311 and Arg341–Lys342 are possibly involved in proteolytic cleavage. The N-terminus of the mature protein is assumed to begin at amino acid residue 108 directly behind the triplet of potential cleavage sites (Lys—Arg—Arg—Thr—Lys—Arg) (Seq ID NO:1) because an arginine residue (Arg104) at the −4 position relative to the proposed cleavage site has been found to enhance cleavage efficiency.

The regions in which the amino acid sequences of furin, Kex1 (*Kluyveromyces lactis*) and Kex2 (*Saccharomyces cerevisiae*) exhibit similarity include parts of the prepro domain, the entire catalytic domain (47% identity if 322 residues) and the entire middle domain (26–31% identity in 138 residues). There is no significant similarity in the transmembrane and cytoplasmic domains, while the Cys-rich domain is not present in the two yeast proteins.

FIG. 3 contains a comparison of the amino acid sequences of (hfur) human furin (Seq ID NO:3), (kex1) Kex1 protease (Seq ID NO:4), (kex2) Kex2 protease (Seq ID NO:5), (ther) thermitase (Seq ID NO:6), (subC) subtilisin Carlsberg (Seq ID NO:7), and (subB) subtilisin BPN (Seq ID NO:8).

On the right-hand side, the numbering of the amino acid residues from the putative N-terminus of the mature enzymes is given, and for furin also along the top. Probably, furin has a prepro segment of 107 residues terminating with the sequence Lys—Arg—Arg—Thr—Lys—Arg (Seq ID NO:1), which has three potential cleavage sites for auto-activation.

(∇) identical residues and (.) conservative substitutions in all six sequences; (:) identical residues in at least four sequences. Pairs of basic residues in furin, Kex1 and Kex2 are indicated in lower case letters. The sequence alignment is taken from a multiple alignment of more than 20 members of the subtilisin family of serine proteases and a superposition of the three-dimensional structures of thermitase, subtilisin Carlsberg and subtilisin BPN' determined by X-ray crystallography. This superposition of three-dimensional structures leads to an extended consensus core, as shown by solid bars, with distances between topologically equivalent Cα atoms of less than 1.5 Å. Secondary structural elements common to all three proteins are indicated as (α) α-helix, (β) β-sheet, (t) β-turn and (s) bend.

Residues known to be involved in substrate or inhibitor binding in thermitase, subtilisin Carlsberg and subtilisin BPN' through main-chain or side-chain interactions are marked with asterisk. Essential residue of the active side (D, H and S) and of the oxyanion hole (N) are underlined. The loops corresponding to the strongest Ca ion binding sites in thermitase are indicated by <===Ca===>.

Boundaries of exons encoding sequences of the presumptive catalytic domain of furin are located behind residues 17, 60, 86, 115, 173, 244, 278 311 and 352.

Figure 4:
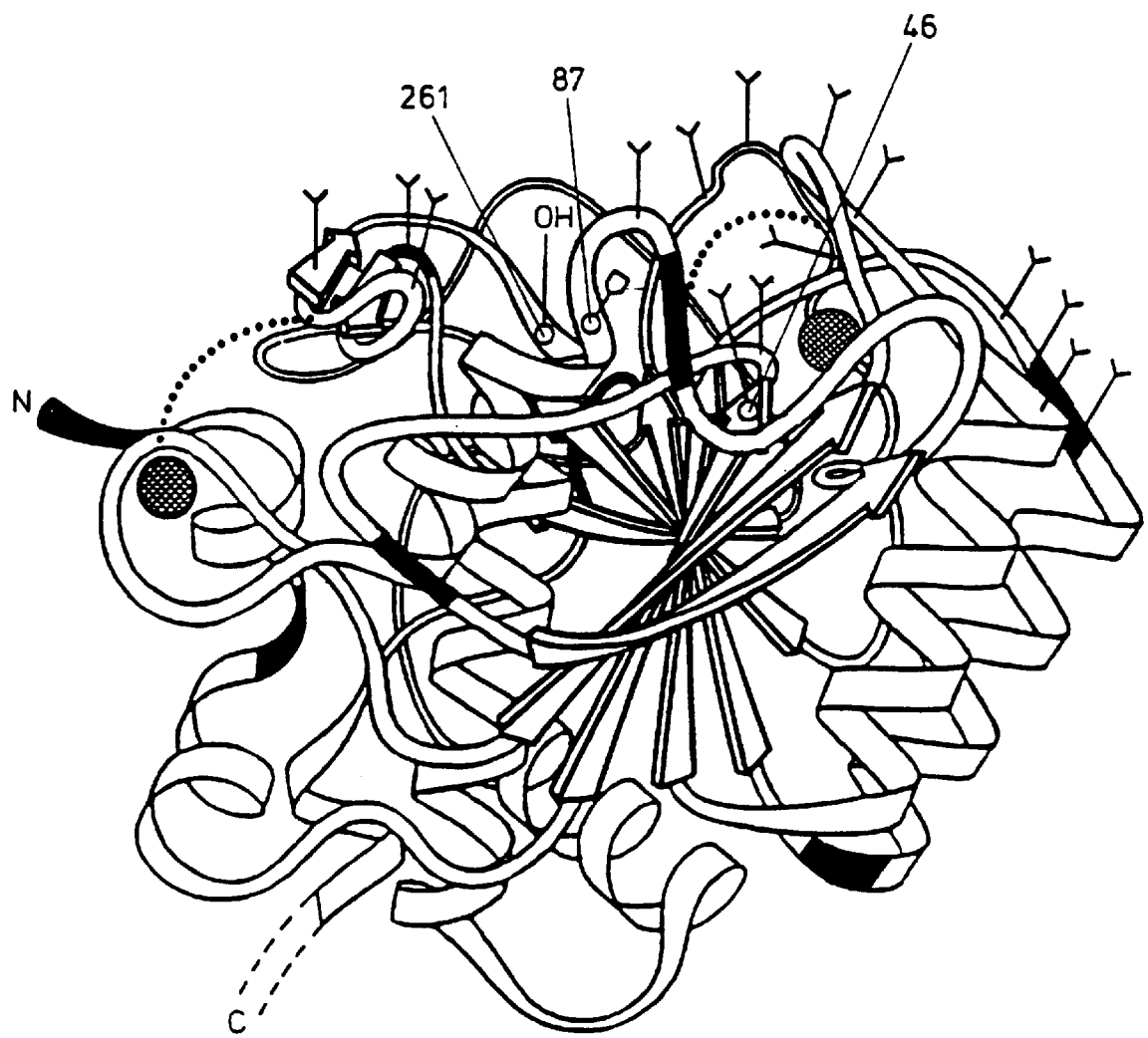
FIG. 4 shows a schematic model of the catalytic domain of furin.

FIG. 4 shows a schematic model of the catalytic domain of furin. The model is based on a ribbon drawing of subtilisin. The active site, consisting of the residues Asp46, His87 and Ser261, is situated at the top centre. The C-terminal extension (dashed) containing additional domains begins at the opposite side of the catalytic domain.

Predicted positions of 8 short inserts (solid black), including an extended N terminus, relative to subtilisin, are seen to be situated in surface loops and in connections between conserved α-helix and β-sheet secondary structural elements.

Predicted positions of two stabilizing calcium ions, Ca1 and Ca2 as in thermitase, are indicated by hatched spheres in the external loops 98–105 and 68–77, respectively. All of the side chain carboxyl groups required for the coordination of these two calcium ions as in thermitase are also present in furin in topologically equivalent residues in these loops; in addition, Asp8 and Asp55 are present to coordinate Ca1 as in thermitase and subtilisin, where in topologically equivalent positions either Gln or Asp are the ligands.

Predicted disulfide bridges Cys104–Cys253 and Cys196–Cys226 (or Cys198–Cys226) are shown in dotted lines.

Negatively charged side chain groups on the substrate binding site (top) of the furin molecule are shown as forked stalks and correspond to residues 46, 47, 84, 121, 123, 126, 150, 151, 152, 192, 194, 199, 241, 248 and 255. Most of these charges are not present in equivalent positions in subtilisins and thermitase. Many of these negatively charged residues could interact directly with paired basic residues in the substrate, as they are probably located in or near the P1 and P2 binding pockets for lysine and/or arginine.

The model described for the catalytic domain of furin also applies to the Kex1 and Kex2 proteases since essentially all of the important elements described above are present in all three proteins.

Figure 5:
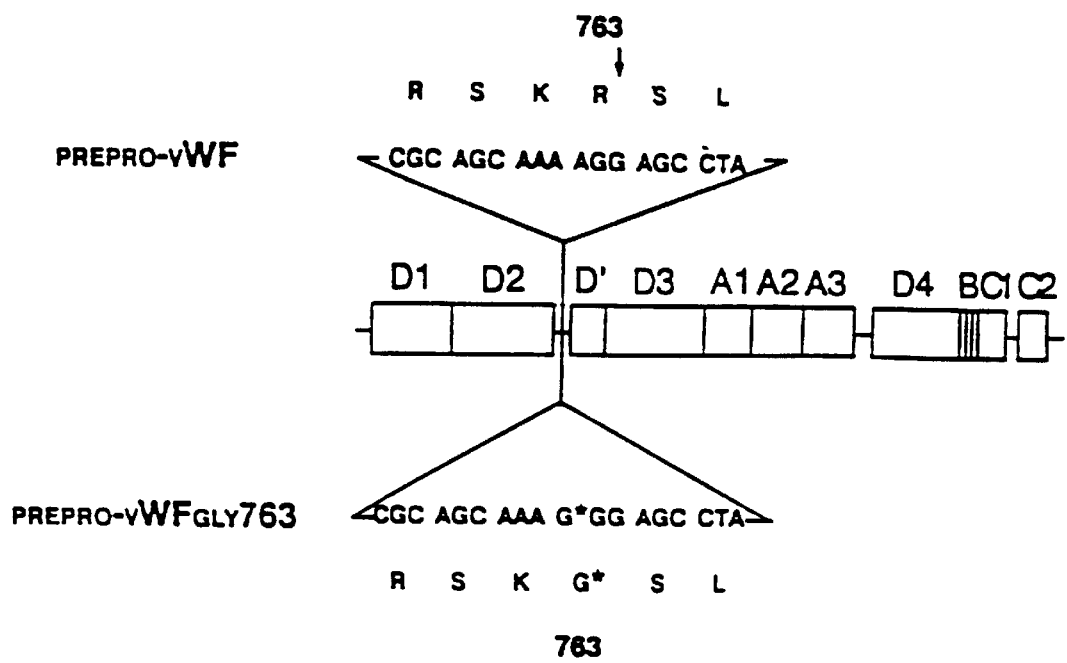
FIG. 5 shows the structural organization of prepro-vWF of wild type von Willebrand Factor (top part) and prepro-vWFgly 763 of the mutant vWFgly 763 (lower part).

FIG. 5 shows diagrammatically the structural organization of prepro-vWF of wild type von Willebrand Factor (top part) and prepro-vWFgly763 of the mutant vWFgly763 (lower part). Internal homologous domains are indicated by open boxes; A1, A2 and A3 represent a triplicated domain; B embodies the homologous domains B1, B2 and B3; C1 and C2 represent a duplicated domain; D1, D2, D3 and D4 represent four repeated domains and D' represents a partly duplicated domain. The solid line indicates the remaining amino acid sequences. The aminoterminal part contains a signal peptide of 22 amino acid residues. The cleavage site after arginine residue at position 763, which consists of a pair of basic amino acid residues, is marked with an arrow. The nucleotide sequence of the DNA region around the cleavage site of prepro-vWF is given (Seq ID NO:10), and the deduced amino acid sequence presented in one-letter notation (SEQ ID NO:9). The nucleotide sequence of the DNA region around the cleavage site of prepro-vWFgly763 is given (SEQ ID NO:11), and the deduced amino acid sequence presented in one letter notation (SEQ ID NO:12). The point mutation in pro-vWFgly 763 (Seq ID NO:11) is marked with an asterisk.

There will now be given an example of a process according to the invention in which the endoproteolytic activity of furin is used in the processing of the precursor of the von Willebrand Factor (pro-vWF) as a substrate. With regard to the structure of prepro, pro and mature vWF, reference is made to Verweij et al., EMBO J. 5, 1986, 1839–1847, and Verweij et al., J.Biol.Chem. 263, 1988, 7921–7924. Pro-vWF consists of a pro-polypeptide (741 amino acid residues) and, at the C terminus, mature vWF (2050 amino acid residues). As explained in the above publications, mature vWF is formed from pro-vWF by proteolytic processing next to the paired basic amino acids Lys762–Arg763, and COS-1 cells are a suitable host for the synthesis of constitutively secreted vWF after transfection of full-length prepro-vWF cDNA. The activity of furin in endo-proteolytic processing was tested for both pro-vWF and the mutant pro-vWFgly763 described by Voorberg et al., EMBO J. 9, 1990, 797–803. The DNA coding for this mutant pro-vWFgly763 contains a guanosine instead of an adenosine in the 2407 position of full-length prepro-vWF cDNA. As a result of this mutation, the cleavage site Lys762–Arg763 of the propolypeptide is replaced by Lys762–Gly763 in the pro-vWF precursor protein mutant.

EXAMPLES

Identification of Translation Products Encoded by Full Length fur cDNA Transfected into COS-1 Cells To further characterize the fur gene produce furin, experiments were performed to synthesize this protein in eukaryotic cells under the control of the SV40 late promotor and to use this material in an approach to elucidate its function. To identify the translation products of the fur gene, an immunological approach was selected. A polyclonal antiserum raised in rabbits to a recombinant furin hybrid protein as described in "Materials and methods" was used. In Western blot analysis of proteins in total lysates of bacteria transformed with pMJ109, pMJ119 or pEW1 DNA, the polyclonal antiserum recognized β-gal-Δfurin1, 336trpE-AS-Δfurin1 and GST-Δfurin2, respectively. In control experiments, the antiserum did not react with the trpE-encoded polypeptide chain of anthralinate synthetase or glutathion-S-transferase. Using this antiserum, Western blot analysis was performed to detect fur gene-encoded proteins in COS-1 cells transfected with pSVLfur. Based upon nucleotide sequence data of fur cDNA, synthesis of a primary translation product with a calculated molecular weight of 87 kDa may be expected. Two proteins with apparent molecular weights of about 90 kDa and 100 kDa, respectively, were detected in transfected COS-1 cells as compared to non-transfected COS-1 cells (results not shown).

The presence of two forms of furin in COS-1 cells transfected with pSVLfur DNA indicates that furin is subject to post-translation al modification. It is possible, that the 100 kDa protein is a glycosylated form of the primary product of about 90 kDa. However, it is also tempting to speculate that the 100 kDa polypeptide would represent the pro-form, while the 90 kDa polypeptide represents mature furin, generated by proteolytic (auto)processing of the peptide bond between residues 107 and 108.

It is noted that non-transfected COS-1 cells also contain small amounts of immunoreactive material with apparent molecular weights of 90, 60 and 40 kDa. Although the identity of these proteins remains to be established, it is conceivable that the 90 kDa protein represents a low amount of endogenous furin.

The data indicate that the transfected fur genetic sequences are indeed transcribed and translated making it possible to test the biological function of the fur products.

Proprotein Processing Activity of Furin

In transfection experiments with 10 μg pSVLvWF DNA, the 360 kDa pro-vWF precursor protein and the 260 kDa mature vWF protein were found in virtually equal proportions in the conditioned medium. The formation of mature vWF in the cells obtained by transfection is attributed to a processing by endogenous furin, which is expressed in COS-1 cells as shown by Northern blot analysis of mRNA isolated for COS-1 cells and by immuno-precipitation analysis with a polyclonal rabbit anti-furin serum.

In similar transfection experiments of COS-1 cells with 10 μg pSVLvWFgly763 DNA, it was found that pro-vWFgly763 was formed and secreted constitutively in the culture medium as a 360 kDa protein. There was no endoproteolytic processing to mature vWF (260 kDa).

The same result was found when a cotransfection of 5 μg pSVLvWFgly763 DNA and 5 μg pSVLfur DNA was carried out. No processing of pro-vWFgly763 to mature vWF was observed.

On the other hand, when COS-1 cells were cotransfected with 5 μg pSVLvWF DNA and 5 μg pSVLfur DNA, a complete processing of pro-vWF to mature vWF was found.

Materials and Methods

Molecular Cloning pSVLfur contains a 4.1 kb full-length fur cDNA fragment, starting 117 nucleotides upstream of the ATG start codon and ending 21 nucleotides downstream of the poly-A addition site cloned into the EcoRI site of pSVL (Wells et al., Nucl. Acids Res. 11, 1983, 7911–7925). In pSVLfur, expression of the fur cDNA sequences is under control of the SV40 late promotor. pMJ109 consists of a 2.2 kb SmaI/SmaI human fur cDNA fragment molecularly cloned into the HindIII site of plasmid pUR291; the 2.2 kb fur cDNA encompasses the carboxyterminal region of furin, which in pMJ109 is fused in phase to the β-galactosidase (β-gal) encoding sequences using the polylinker region constructed just in front of the stop codon in lacZ. pMJ119 consists of the same 2.2 kb fur cDNA fragment but here molecularly cloned into the SmaI site of plasmid pATH1, which results in the in phase fusion of the furin sequences to the first 336 amino acid residues of the trpE-encoded portion of anthranilate synthetase (336trpE-AS). Finally, in case of pEW1, a 3.5 kb BglII/EcoRI fur cDNA fragment is cloned into pGEX-3X and fused in phase to glutathion-S-transferase (GST).

Upon proper induction of protein synthesis in bacteria transformed with pMJ109, pMJ119 or pEW1, production of relatively large quantities of β-gal-Δ-furin1 (MW 170 kDa), 336trpE-AS-Δfurin1 (MW 90 kDa) and GST-Δfurin2 (MW 100 kDa), respectively, was observed.

Preparation of Polyclonal Anti-Furin Antibodies and Immunoblotting

Polyclonal anti-furin antibodies were raised in rabbits to the β-gal-Δ-furin1 hybrid protein synthesized in bacteria transformed by pMJ109. For immunizations, partially purified hybrid protein preparations were used. Upon size fractionation of the bacterial proteins by SDA-PAGE, the gel region containing the hybrid protein was excised and the protein content removed electrophoretically. Western blotting experiments with extracts of transfected COS-1 cells were performed as follows. COS-1 cells transfected with 10 μg of pSVLfur DNA were maintained 48 hr post-transfection in serum-free medium. At this time, the cells were washed twice with 10 mM sodium phosphate (pH 7.4), 0.14 M NaCl and then lyzed in "immunoprecipitation buffer (IBP)" consisting of 10 mM Tris-HCl (pH 7.8), 150 mM NaCl, 5 mM-EDTA, 1% (v/v) Nonidet P-40, 10 mM benzamidine, 5 mM N-ethylmaleimide and 1 mM phenylmethylsulfonyl fluoride (PMSF). An aliquot of the cell extract was run under reducing conditions on a 8% (w/v) SDS-polyacrylamide gel and, subsequently, proteins were transferred to nitrocellulose (Schleicher and Schuell). Detection of furin was performed by incubating the blot with the rabbit anti-furin serum described above.

DNA Transfection, Radiolabeling of Cells and Immuno-Precipitation Analysis

Monkey kidney COS-1 cells were propagated in Iscove's modified minimal medium, supplemented with fetal calf serum (10% v/v) and antibiotics [penicillin (100 U/ml) and streptomycin (100 μg/ml)]. Twenty four hours upon seeding, the semi-confluent cells were transfected with 20 μg of DNA in 2 ml of Iscove's modified minimal medium, supplemented with 200 μg/ml DEAE-dextran. The transfection procedure used included a chloroquine shock (Luthman and Magnusson, Nucl. Acids Res. 11, 1983, 1295–1308). After transfection, cells were maintained in the medium described above for 48 hours. Prior to radiolabelling, medium was removed and the cells incubated for 1 h in RPMI medium, lacking methionine. Subsequently, cells were labelled for 4 hours in the presence of [$^{35}$S]methionine (50 μCi/ml, specific activity >800 Ci/mmol), followed by a chase of 14 hours with unlabelled methionine (final concentration 1 mM). After centrifugation for 5 min at 13,000×g, the labelled culture media were adjusted to 1×IPB. Preclearance of the media was performed by incubating twice with gelatin-Sepharose and, subsequently, with preformed complexes of rabbit pre-immune serum with Protein A-Sepharose. Immunoprecipitation of radiolabelled vWF-related proteins was carried out by preformed complexes of an IgG preparation, derived from rabbit anti-vWF (Dakopatts, Glostrup, Denmark) with Protein A-Sepharose. Immunoprecipitates were extensively washed with IPB and pelleted through a discontinuous 10–20% (w/v) sucrose gradient dissolved in IPB supplemented with 0.5% desoxycholate and 10 mM Tris-HCl (pH 7.8), respectively. Immunoprecipitates were analysed under reducing conditions on a 5% SDS-polyacrylamide gel.

We claim:

1. A process for the in vitro cleavage of protein which comprises treating the protein with furin in the presence of $Ca^{2+}$ ions.

2. A process as claimed in claim 1, in which the treatment is carried out at a pH of 5–7.5.

3. A process as claimed in claim 1, in which the treatment is carried out at a calcium concentration of 1–10 mM.

4. A process as claimed in claim 1, in which the treatment is carried out in presence of o-phenanthroline or agent for binding ions of heavy metals other than calcium.

5. A process as claimed in claim 1, in which the treatment is carried out at a temperature of 20–50° C.

6. A process as claimed in claim 1, in which the treatment is applied to a protein precursor.

7. A mammalian cell containing heterologous DNA coding for furin and which expresses furin.

8. A process as claimed in claim 2, in which the treatment is carried out at a calcium concentration of 1–10 mM.

9. A process as claimed in 2, in which the treatment is carried out in presence of o-phenanthroline or agent for binding ions of heavy metals other than calcium.

10. A process as claimed in 3, in which the treatment is carried out in presence of o-phenanthroline or agent for binding ions of heavy metals other than calcium.

11. A process as claimed in 8, in which the treatment is carried out in presence of o-phenanthroline or agent for binding ions of heavy metals other than calcium.

12. A process as claimed in 2, in which the treatment is carried out at a temperature of 20–50° C.

13. A process as claimed in 3, in which the treatment is carried out at a temperature of 20–50° C.

14. A process as claimed in 8, in which the treatment is carried out at a temperature of 20–50° C.

15. A process as claimed in 4, in which the treatment is carawed out at a temperature of 20–50° C.

16. A process as claimed in 9, in which the treatment is carried out at a temperature of 20–50° C.

17. A process as claimed in 10, in which the treatment is carried out at a temperature of 20–50° C.

18. A process as claimed in 11, in which the treatment is carried out at a temperature of 20–50° C.

19. A process as claimed in claim 2, in which the treatment is applied to a protein precursor.

20. A process as claimed in claim 3, in which the treatment is applied to a protein precursor.

21. A process as claimed in claim 8, in which the treatment is applied to a protein precursor.

22. A process as claimed in claim 4, in which the treatment is applied to a protein precursor.

23. A process as claimed in claim 9, in which the treatment is applied to a protein precursor.

24. A process as claimed in claim 10, in which the treatment is applied to a protein precursor.

25. A process as claimed in claim 11, in which the treatment is applied to a protein precursor.

26. A process as claimed in claim 5, in which the treatment is applied to a protein precursor.

27. A process as claimed in claim 12, in which the treatment is applied to a protein precursor.

28. A process as claimed in claim 13, in which the treatment is applied to a protein precursor.

29. A process as claimed in claim 14, in which the treatment is applied to a protein precursor.

30. A process as claimed in claim 15, in which the treatment is applied to a protein precursor.

31. A process as claimed in claim 16, in which the treatment is applied to a protein precursor.

32. A process as claimed in claim 17, in which the treatment is applied to a protein precursor.

33. A process as claimed in claim 18, in which the treatment is applied to a protein precursor.

34. A process as claimed in claim 1 in which the treatment is applied to the precursor of a protein selected from a group consisting of polypeptide hormones, growth factors, toxins and enzymes.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Lys Arg Arg Thr Lys Arg
1               5

(2) INFORMATION FOR SEQ ID NO:2:

(i) SEQUENCE CHARACTERISTICS:
      (A) LENGTH: 794 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
                20                  25                  30

Thr Trp Ala Val Arg Ile Pro Gly Gly Pro Ala Val Ala Asn Ser Val
                35                  40                  45

Ala Arg Lys His Gly Phe Leu Asn Leu Gly Gln Ile Phe Gly Asp Tyr
        50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
                100                 105                 110

Pro Thr Asp Pro Lys Phe Pro Gln Gln Trp Tyr Leu Ser Gly Val Thr
                115                 120                 125

-continued

```
Gln Arg Asp Leu Asn Val Lys Ala Ala Trp Ala Gln Gly Tyr Thr Gly
        130                 135                 140
 His Gly Ile Val Val Ser Ile Leu Asp Asp Gly Ile Glu Lys Asn His
145                 150                 155                 160
Pro Asp Leu Ala Gly Asn Tyr Asp Pro Gly Ala Ser Phe Asp Val Asn
                165                 170                 175
Asp Gln Asp Pro Asp Pro Gln Pro Arg Tyr Thr Gln Met Asn Asp Asn
            180                 185                 190
Arg His Gly Thr Arg Cys Ala Gly Glu Val Ala Ala Val Ala Asn Asn
            195                 200                 205
Gly Val Cys Gly Val Gly Val Ala Tyr Asn Ala Arg Ile Gly Gly Val
        210                 215                 220
Arg Met Leu Asp Gly Glu Val Thr Asp Ala Val Glu Ala Arg Ser Leu
225                 230                 235                 240
Gly Leu Asn Pro Asn His Ile His Ile Tyr Ser Ala Ser Trp Gly Pro
                245                 250                 255
Glu Asp Asp Gly Lys Thr Val Asp Gly Pro Ala Arg Leu Ala Glu Glu
            260                 265                 270
Ala Phe Phe Arg Gly Val Ser Gln Gly Arg Gly Gly Leu Gly Ser Ile
            275                 280                 285
Phe Val Trp Ala Ser Gly Asn Gly Gly Arg Glu His Asp Ser Cys Asn
        290                 295                 300
Cys Asp Gly Tyr Thr Asn Ser Ile Tyr Thr Leu Ser Ile Ser Ser Ala
305                 310                 315                 320
Thr Gln Phe Gly Asn Val Pro Trp Tyr Ser Glu Ala Cys Ser Ser Thr
                325                 330                 335
Leu Ala Thr Thr Tyr Ser Ser Gly Asn Gln Asn Glu Lys Gln Ile Val
            340                 345                 350
Thr Thr Asp Leu Arg Gln Lys Cys Thr Glu Ser His Thr Gly Thr Ser
            355                 360                 365
Ala Ser Ala Pro Leu Ala Ala Gly Ile Ile Ala Leu Thr Leu Glu Ala
        370                 375                 380
Asn Lys Asn Leu Thr Trp Arg Asp Met Gln His Leu Val Val Gln Thr
385                 390                 395                 400
Ser Lys Pro Ala His Leu Asn Ala Asn Asp Trp Ala Thr Asn Gly Val
                405                 410                 415
Gly Arg Lys Val Ser His Ser Tyr Gly Tyr Gly Leu Leu Asp Ala Gly
            420                 425                 430
Ala Met Val Ala Leu Ala Gln Asn Trp Thr Thr Val Ala Pro Gln Arg
            435                 440                 445
Lys Cys Ile Ile Asp Ile Leu Thr Glu Pro Lys Asp Ile Gly Lys Arg
        450                 455                 460
Leu Glu Val Arg Lys Thr Val Thr Ala Cys Leu Gly Glu Pro Asn His
465                 470                 475                 480
Ile Thr Arg Leu Glu His Ala Gln Ala Arg Leu Thr Leu Ser Tyr Asn
                485                 490                 495
Arg Arg Gly Asp Leu Ala Ile His Leu Val Ser Pro Met Gly Thr Arg
            500                 505                 510
Ser Thr Leu Leu Ala Ala Arg Pro His Asp Tyr Ser Ala Asp Gly Phe
            515                 520                 525
Asn Asp Trp Ala Phe Met Thr Thr His Ser Trp Asp Glu Asp Pro Ser
        530                 535                 540
Gly Glu Trp Val Leu Glu Ile Glu Asn Thr Ser Glu Ala Asn Asn Tyr
545                 550                 555                 560
```

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
                580                 585                 590

Ser Gln Ala Cys Val Val Cys Glu Glu Gly Phe Ser Leu His Gln Lys
                595                 600                 605

Ser Cys Val Gln His Cys Pro Pro Gly Phe Ala Pro Gln Val Leu Asp
                610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
                660                 665                 670

Gln Thr Cys Ser Arg Gln Ser Gln Ser Ser Arg Glu Ser Pro Pro Gln
                675                 680                 685

Gln Gln Pro Pro Arg Leu Pro Pro Glu Val Glu Ala Gly Gln Arg Leu
                690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
                740                 745                 750

Asp Arg Gly Leu Ile Ser Tyr Lys Gly Leu Pro Pro Glu Ala Trp Gln
                755                 760                 765

Glu Glu Cys Pro Ser Asp Ser Glu Asp Glu Gly Arg Gly Glu Arg
                770                 775                 780

Thr Ala Phe Ile Lys Asp Gln Ser Ala Leu
785                 790

(2) INFORMATION FOR SEQ ID NO:3:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Asp Val Tyr Gln Glu Pro Thr Asp Pro Lys Phe Pro Gln Gln Trp Tyr
1               5                   10                  15

Leu Ser Gly Val Thr Gln Arg Asp Leu Asn Val Lys Ala Ala Trp Ala
                20                  25                  30

Gln Gly Tyr Thr Gly His Gly Ile Val Val Ser Ile Leu Asp Asp Gly
                35                  40                  45

Ile Glu Lys Asn His Pro Asp Leu Ala Gly Asn Tyr Asp Pro Gly Ala
                50                  55                  60

Ser Phe Asp Val Asn Asp Gln Asp Pro Asp Pro Gln Pro Arg Tyr Thr
65              70                  75                  80

Gln Met Asn Asp Asn Arg His Gly Thr Arg Cys Ala Gly Glu Val Ala
                85                  90                  95

Ala Val Ala Asn Asn Gly Val Cys Gly Val Gly Val Ala Tyr Asn Ala
                100                 105                 110

```
Arg Ile Gly Gly Val Arg Met Leu Asp Gly Glu Val Thr Asp Ala Val
            115                 120                 125

Glu Ala Arg Ser Leu Gly Leu Asn Pro Asn His Ile His Ile Tyr Ser
        130                 135                 140

Ala Ser Trp Gly Pro Glu Asp Asp Gly Lys Thr Val Asp Gly Pro Ala
145                 150                 155                 160

Arg Leu Ala Glu Glu Ala Phe Phe Arg Gly Val Ser Gln Gly Arg Gly
                165                 170                 175

Gly Leu Gly Ser Ile Phe Val Trp Ala Ser Gly Asn Gly Gly Arg Glu
                180                 185                 190

His Asp Ser Cys Asn Cys Asp Gly Tyr Thr Asn Ser Ile Tyr Thr Leu
                195                 200                 205

Ser Ile Ser Ser Ala Thr Gln Phe Gly Asn Val Pro Trp Tyr Ser Glu
            210                 215                 220

Ala Cys Ser Ser Thr Leu Ala Thr Thr Tyr Ser Ser Gly Asn Gln Asn
225                 230                 235                 240

Glu Lys Gln Ile Val Thr Thr Asp Leu Arg Gln Lys Cys Thr Glu Ser
                245                 250                 255

His Thr Gly Thr Ser Ala Ser Ala Pro Leu Ala Ala Gly Ile Ile Ala
                260                 265                 270

Leu Thr Leu Glu Ala Asn Lys Asn Leu Thr Trp Arg Asp Met Gln His
        275                 280                 285

Leu Val Val Gln Thr Ser Lys Pro Ala His Leu Asn Ala Asn Asp Trp
290                 295                 300

Ala Thr Asn Gly Val Gly Arg Lys Val Ser His Ser Tyr Gly Tyr Gly
305                 310                 315                 320

Leu Leu Asp Ala Gly Ala Met Val Ala Leu Ala Gln Asn Trp Thr Thr
                325                 330                 335

Val Ala Pro Gln Arg Lys Cys Ile Ile Asp Ile Leu Thr Glu Pro Lys
                340                 345                 350

Asp Ile Gly Lys Arg
        355

(2) INFORMATION FOR SEQ ID NO:4:

(i) SEQUENCE CHARACTERISTICS:
        (A) LENGTH: 353 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Arg Ile Leu Phe Asn Ile Ser Asp Pro Leu Phe Asp Gln Gln Trp His
1                   5                   10                  15

Leu Ile Asn Pro Asn Tyr Pro Gly Asn Asp Val Asn Val Thr Gly Leu
            20                  25                  30

Trp Lys Glu Asn Ile Thr Gly Tyr Gly Val Val Ala Ala Leu Val Asp
        35                  40                  45

Asp Gly Leu Asp Tyr Glu Asn Glu Asp Leu Lys Asp Asn Phe Cys Val
    50                  55                  60

Glu Gly Ser Trp Asp Phe Asn Asp Asn Asn Pro Leu Pro Lys Pro Arg
65                  70                  75                  80

Leu Lys Asp Asp Tyr His Gly Thr Arg Cys Ala Gly Glu Ile Ala Ala
                85                  90                  95

Phe Arg Asn Asp Ile Cys Gly Val Gly Val Ala Tyr Asn Ser Lys Val
```

```
                100                 105                 110
Ser Gly Ile Arg Ile Leu Ser Gly Gln Ile Thr Ala Glu Asp Ala
                115                 120                 125

Ala Ser Leu Ile Tyr Gly Leu Asp Val Asn Asp Ile Tyr Ser Cys Ser
            130                 135                 140

Trp Gly Pro Ser Asp Asp Gly Lys Thr Met Gln Ala Pro Asp Thr Leu
145                 150                 155                 160

Val Lys Lys Ala Ile Ile Lys Gly Val Thr Glu Gly Arg Asp Ala Lys
                165                 170                 175

Gly Ala Leu Tyr Val Phe Ala Ser Gly Asn Gly Gly Met Phe Gly Asp
                180                 185                 190

Ser Cys Asn Phe Asp Gly Tyr Thr Asn Ser Ile Phe Ser Ile Thr Val
                195                 200                 205

Gly Ala Ile Asp Trp Lys Gly Leu His Pro Pro Tyr Ser Glu Ser Cys
            210                 215                 220

Ser Ala Val Met Val Val Thr Tyr Ser Ser Gly Ser Gly Asn Tyr Ile
225                 230                 235                 240

Lys Thr Thr Asp Leu Asp Glu Lys Cys Ser Asn Thr His Gly Gly Thr
                245                 250                 255

Ser Ala Ala Ala Pro Leu Ala Ala Gly Ile Tyr Thr Leu Val Leu Glu
            260                 265                 270

Ala Asn Pro Asn Leu Thr Trp Arg Asp Val Gln Tyr Leu Ser Ile Leu
            275                 280                 285

Ser Ser Glu Glu Ile Asn Pro His Asp Gly Lys Trp Gln Asp Thr Ala
            290                 295                 300

Met Gly Lys Arg Tyr Ser His Thr Tyr Gly Phe Gly Lys Leu Asp Ala
305                 310                 315                 320

Tyr Asn Ile Val His Met Ala Lys Ser Trp Ile Asn Val Asn Pro Gln
                325                 330                 335

Gly Trp Leu Tyr Leu Pro Thr Ile Val Glu Lys Gln Ser Ile Ser Asn
                340                 345                 350

Ser
```

(2) INFORMATION FOR SEQ ID NO:5:

(i) SEQUENCE CHARACTERISTICS:
        (A) LENGTH: 355 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Glu Asp Lys Leu Ser Ile Asn Asp Pro Leu Phe Glu Arg Gln Trp His
1               5                   10                  15

Leu Val Asn Pro Ser Phe Pro Gly Ser Asp Ile Asn Val Leu Asp Leu
                20                  25                  30

Trp Tyr Asn Asn Ile Thr Gly Ala Gly Val Val Ala Ala Ile Val Asp
                35                  40                  45

Asp Gly Leu Asp Tyr Glu Asn Glu Asp Leu Lys Asp Asn Phe Cys Ala
            50                  55                  60

Glu Gly Ser Trp Asp Phe Asn Asp Asn Thr Asn Leu Pro Lys Pro Arg
65              70                  75                  80

Leu Ser Asp Asp Tyr His Gly Thr Arg Cys Ala Gly Glu Ile Ala Ala
                85                  90                  95
```

```
Lys Lys Gly Asn Asn Phe Cys Gly Val Gly Val Gly Tyr Asn Ala Lys
                100                 105                 110
Ile Ser Gly Ile Arg Ile Leu Ser Gly Asp Ile Thr Thr Glu Asp Glu
            115                 120                 125
Ala Ala Ser Leu Ile Tyr Gly Leu Asp Val Asn Asp Ile Tyr Ser Cys
        130                 135                 140
Ser Trp Gly Pro Ala Asp Asp Gly Arg His Leu Gln Gly Pro Ser Asp
145                 150                 155                 160
Leu Val Lys Lys Ala Leu Val Lys Gly Val Thr Glu Gly Arg Asp Ser
                165                 170                 175
Lys Gly Ala Ile Tyr Val Phe Ala Ser Gly Asn Gly Gly Thr Arg Gly
                180                 185                 190
Asp Asn Cys Asn Tyr Asp Gly Tyr Thr Asn Ser Ile Tyr Ser Ile Thr
            195                 200                 205
Ile Gly Ala Ile Asp His Lys Asp Leu His Pro Pro Tyr Ser Glu Gly
        210                 215                 220
Cys Ser Ala Val Met Ala Val Thr Tyr Ser Ser Gly Ser Gly Glu Tyr
225                 230                 235                 240
Ile His Ser Ser Asp Ile Asn Gly Arg Cys Ser Asn Ser His Gly Gly
                245                 250                 255
Thr Ser Ala Ala Ala Pro Leu Ala Ala Gly Val Tyr Thr Leu Leu Leu
                260                 265                 270
Glu Ala Asn Pro Asn Leu Thr Trp Arg Asp Val Gln Tyr Leu Ser Ile
            275                 280                 285
Leu Ser Ala Val Gly Leu Glu Lys Asn Ala Asp Gly Asp Trp Arg Asp
        290                 295                 300
Ser Ala Met Gly Lys Lys Tyr Ser His Arg Tyr Gly Phe Gly Lys Ile
305                 310                 315                 320
Asp Ala His Lys Leu Ile Glu Met Ser Lys Thr Trp Glu Asn Val Asn
                325                 330                 335
Ala Gln Thr Trp Phe Tyr Leu Pro Thr Leu Tyr Val Ser Gln Ser Thr
                340                 345                 350
Asn Ser Thr
        355

(2) INFORMATION FOR SEQ ID NO:6:

(i) SEQUENCE CHARACTERISTICS:
        (A) LENGTH: 278 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Tyr Thr Pro Asn Asp Pro Tyr Phe Ser Ser Arg Gln Tyr Gly Pro Gln
1               5                   10                  15
Lys Ile Gln Ala Pro Gln Ala Trp Asp Ile Ala Glu Gly Ser Gly Ala
            20                  25                  30
Lys Ile Ala Ile Val Asp Thr Gly Val Gln Ser Asn His Pro Asp Leu
        35                  40                  45
Ala Gly Lys Val Val Gly Gly Trp Asp Phe Val Asp Asn Asp Ser Thr
    50                  55                  60
Pro Gln Asn Gly Asn Gly His Gly Thr His Cys Ala Gly Ile Ala Ala
65                  70                  75                  80
Ala Val Thr Asn Asn Ser Thr Gly Ile Ala Gly Thr Ala Pro Lys Ala
```

```
                      85                  90                  95
Ser Ile Leu Ala Val Arg Val Leu Asp Asn Ser Gly Ser Gly Thr Trp
                100                 105                 110
Thr Ala Val Ala Asn Gly Ile Thr Tyr Ala Ala Asp Gln Gly Ala Lys
            115                 120                 125
Val Ile Ser Leu Ser Leu Gly Gly Thr Val Gly Asn Ser Gly Leu Gln
        130                 135                 140
Gln Ala Val Asn Tyr Ala Trp Asn Lys Gly Ser Val Val Ala Ala
145                 150                 155                 160
Ala Gly Asn Ala Gly Asn Thr Ala Pro Asn Tyr Pro Ala Tyr Tyr Ser
                165                 170                 175
Asn Ala Ile Ala Val Ala Ser Thr Asp Gln Asn Asp Asn Lys Ser Ser
                180                 185                 190
Phe Ser Thr Tyr Gly Ser Val Val Asp Val Ala Ala Pro Gly Ser Trp
            195                 200                 205
Ile Tyr Ser Thr Tyr Pro Thr Ser Thr Tyr Ala Ser Leu Ser Gly Thr
        210                 215                 220
Ser Met Ala Thr Pro His Val Ala Gly Val Ala Gly Leu Leu Ala Ser
225                 230                 235                 240
  Gln Gly Arg Ser Ala Ser Asn Ile Arg Ala Ala Ile Glu Asn Thr Ala
                245                 250                 255
Asp Lys Ile Ser Gly Gly Thr Tyr Trp Ala Lys Gly Arg Val Asn Ala
                260                 265                 270
Tyr Lys Ala Val Gln Tyr
            275

(2) INFORMATION FOR SEQ ID NO:7:

(i) SEQUENCE CHARACTERISTICS:
        (A) LENGTH: 274 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ala Gln Thr Val Pro Tyr Gly Ile Pro Leu Ile Lys Ala Asp Lys Val
1               5                   10                  15
Gln Ala Gln Gly Phe Lys Gly Ala Asn Val Lys Val Ala Val Leu Asp
            20                  25                  30
Thr Gly Ile Gln Ala Ser His Pro Asp Leu Asn Val Val Gly Gly Ala
        35                  40                  45
Ser Phe Val Ala Gly Glu Ala Tyr Asn Thr Asp Gly Asn Gly His Gly
    50                  55                  60
Thr His Val Ala Gly Thr Val Ala Ala Leu Asp Asn Thr Thr Gly Val
65                  70                  75                  80
Leu Gly Val Ala Pro Ser Val Ser Leu Tyr Ala Val Lys Val Leu Asn
                85                  90                  95
Ser Ser Gly Ser Gly Thr Tyr Ser Gly Ile Val Ser Gly Ile Glu Trp
                100                 105                 110
Ala Thr Thr Asn Gly Met Asp Val Ile Asn Met Ser Leu Gly Gly Pro
            115                 120                 125
Ser Gly Ser Thr Ala Met Lys Gln Ala Val Asp Asn Ala Tyr Ala Arg
        130                 135                 140
Gly Val Val Val Val Ala Ala Gly Asn Ser Gly Ser Ser Gly Asn
145                 150                 155                 160
```

```
Thr Asn Thr Ile Gly Tyr Pro Ala Lys Tyr Asp Ser Val Ile Ala Val
            165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
            195                 200                 205

Pro Thr Ser Thr Tyr Ala Thr Leu Asn Gly Thr Ser Met Ala Ser Pro
            210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
            245                 250                 255

Gly Ser Ser Phe Tyr Tyr Gly Lys Gly Leu Ile Asn Val Glu Ala Ala
            260                 265                 270

Ala Gln (2) INFORMATION FOR SEQ ID NO:8:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
            50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
             85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
            130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
            165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
            210                 215                 220

Pro His Val Ala Gly Ala Ala Ala Leu Ile Leu Ser Lys His Pro Asn
```

```
                225                 230                 235                 240
Trp Thr Asn Thr Gln Val Arg Ser Ser Leu Glu Asn Thr Thr Thr Lys
                    245                 250                 255

Leu Gly Asp Ser Phe Tyr Tyr Gly Lys Gly Leu Ile Asn Val Gln Ala
            260                 265                 270

Ala Ala Gln
        275

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Arg Ser Lys Arg Ser Leu
1               5

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGCAGCAAAA GGAGCCTA                                             18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCAGCAAAG GGAGCCTA                                             18

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Arg Ser Lys Gly Ser Leu
1               5
```